United States Patent [19]

Wagner

[11] 4,322,363

[45] Mar. 30, 1982

[54] METHOD FOR MAKING DIBUTYLTIN DIFLUORIDE

[75] Inventor: William E. Wagner, Verona, Pa.

[73] Assignee: PPG Industries, Inc., Pittsburgh, Pa.

[21] Appl. No.: 172,906

[22] Filed: Jul. 28, 1980

[51] Int. Cl.³ .............................................. C07F 7/22
[52] U.S. Cl. ................................................. 260/429.7
[58] Field of Search ..................................... 260/429.7

[56] References Cited

U.S. PATENT DOCUMENTS 4,191,698  3/1980  Gitlitz et al. ...................... 260/429.7
4,254,046  3/1981  Franz ................................. 260/429.7

OTHER PUBLICATIONS

Chemical Reviews, vol. 60, p. 502 (1960).
Krause, Chem. Ber. 51, 1447 (1918).
ACTA Pharm. Jugoslav 18, 3,117 (1968) Chem. Abstracts 73:8797C.
Hobbs and Tobias, Inorg. Chem. 9, 1037 (1970).
Lewchuk, Inorg. Chem. 11, 43 (1972).

*Primary Examiner*—Helen M. S. Sneed
*Attorney, Agent, or Firm*—Donna L. Seidel

[57] ABSTRACT

A method for making dialkyltin difluorides by reacting the corresponding dialkyltin diacetate with hydrogen fluoride is disclosed.

5 Claims, No Drawings

METHOD FOR MAKING DIBUTYLTIN DIFLUORIDE

BACKGROUND OF THE INVENTION

1. Field of the Invention

The present invention relates generally to the art of synthesizing dialkyltin difluorides and more particularly, to the art of synthesizing a dialkyltin difluoride from a starting material other than a dialkyltin dichloride.

2. The Prior Art

Hobbs and Tobias disclose the reaction of dimethyltin oxide with aqueous hydrofluoric acid to form dimethyltin difluoride in *Inorganic Chemistry* vol. 9, p. 1037 (1970). Lewchuck et al disclose the preparation of dimethyltin difluoride by reacting dimethyltin dichloride with aqueous hydrofluoric acid in *Inorganic Chemistry*, vol. 11 p. 43 (1972).

In U.S. Pat. No. 4,254,046, Franz et al disclose the conversion of dimethyltin dichloride to dimethyltin difluoride using aqueous solutions of alkali metal or ammonium fluoride salts.

SUMMARY OF THE INVENTION

The present invention provides a method for making a dialkyltin difluoride, specifically dibutyltin difluoride, from the corresponding diacetate. Dibutyltin diacetate is reacted with hydrogen fluoride to form dibutyltin difluoride.

DESCRIPTION OF THE PREFERRED EMBODIMENT

Dialkyltin diacetate, preferably dibutyltin diacetate, is reacted with hydrogen fluoride, preferably in approximately chemically equivalent proportion. The reaction may be conducted in aqueous or organic, preferably alcoholic, solution. The hydrogen fluoride may be in the gaseous phase.

The reaction mixture fumes during the formation of dibutyltin difluoride, which is preferably carried out at ambient temperatures. When substantially chemically equivalent amounts of dibutyltin diacetate and hydrogen fluoride are reacted, the dibutyltin difluoride product is obtained as a powder, which is preferably dried.

In one preferred embodiment of the present invention, liquid dibutyltin diacetate is added at ambient temperature to an aqueous solution containing about 70 percent hydrogen fluoride. The volumes of both reactants are chosen to provide a substantially stoichiometric proportion. The reaction mixture fumes, losing water and acetate in the process, yielding dibutyltin difluoride in the form of a wet powder. The reaction product is preferably dried at moderate temperatures, typically 100° to 150° F. (about 38°–66° C.).

In another preferred embodiment, liquid dibutyltin diacetate is added at ambient temperature to a solution containing about 30 percent hydrogen fluoride in methanol. Reaction of substantially chemically equivalent proportions of the tin compound and the fluoride produces dibutyltin difluoride in the form of a wet powder, which is preferably dried.

The dibutyltin difluoride powder is particularly useful as a coating reactant for the pyrolytic deposition of tin oxide films, especially onto glass substrates. The dibutyltin difluoride may be used in the powder form for chemical vapor deposition or powder coating, or may be dissolved in an appropriate solvent for spray application in a pyrolytic process.

The present invention will be further understood from the descriptions of specific examples which follow.

EXAMPLE I

One gallon (3.8 liters) of dibutyltin diacetate is added at ambient temperature to 970 cubic centimeters of 70 percent hydrogen fluoride in water. The reaction mixture fumes for about 15 minutes with the resultant loss of water and acetate. Dibutyltin difluoride is obtained in the form of a wet powder which is dried at 100° to 150° F. (about 38°–66° C.) for about 2 to 3 hours to yield about 1900 grams of dibutyltin difluoride in the form of a dry powder.

EXAMPLE II

A volume of 4.2 gallons (15.9 liters) of 30 percent hydrogen fluoride in methanol is added to 5 gallons (18.9 liters) of dibutyltin diacetate, forming a powder of dibutyltin difluoride. The powder is dried as in the previous example and then ground to an average particle size of 500 to 600 microns for use as a coating reactant to deposit a tin oxide film on glass by pyrolysis.

The above examples illustrate the present invention which may be carried out at various temperatures with the reactants in other proportions and the product obtained in the alternate forms. The dibutyltin difluoride prepared according to the present invention is a preferred coating reactant because it contains no residual chloride which can cause deleterious effects in a tin oxide film forming process. The scope of the invention is defined by the following claims.

I claim:

1. A method for making dialkyltin difluoride which comprises reacting the corresponding dialkyltin diacetate in liquid form and substantially stoichiometric proportion with hydrogen fluoride.

2. The method according to claim 1, wherein the reaction is carried out in aqueous solution.

3. The method according to claim 2, wherein dibutyltin diacetate is reacted with concentrated aqueous hydrofluoric acid to form dibutyltin difluoride in the form of a wet powder.

4. The method according to claim 1, wherein dibutyltin diacetate is reacted with hydrogen fluoride in solution in methanol.

5. The method according to claim 1, wherein the reaction is carried out at ambient temperatures.

* * * * *